United States Patent [19]

Butler

[11] 4,111,943

[45] Sep. 5, 1978

[54] 3-(THIENYLOXY)PYRIDINES AND METHODS FOR THEIR PRODUCTION

[75] Inventor: Donald Eugene Butler, Ann Arbor, Mich.

[73] Assignee: Warner-Lambert Company, Morris Plains, N.J.

[21] Appl. No.: 789,031

[22] Filed: Apr. 20, 1977

[51] Int. Cl.$^2$ ............................................. C07D 417/02
[52] U.S. Cl. ............................... 260/294.8 D; 424/263
[58] Field of Search ................................. 260/294.8 D

[56] References Cited

U.S. PATENT DOCUMENTS 3,429,689   2/1969   Duerr et al. ..................... 260/297 R

OTHER PUBLICATIONS

Butler et al., J. Med. Chem., vol. 14(7), pp. 575–579 (1971).
Renshaw et al., J. Am. Chem. Soc., vol. 59(2), pp. 297–301, Feb. (1937).

*Primary Examiner*—Alan L. Rotman
*Attorney, Agent, or Firm*—Stephen Raines; David B. Ehrlinger; Frank S. Chow

[57] ABSTRACT

3-(Thienyloxy)pyridines and acid-addition salts thereof, which are useful as pharmacological agents, especially in the area of psychostimulants, are disclosed. These compounds can be produced by reacting a halothiophene with a metallic salt of 3-hydroxypyridine.

4 Claims, No Drawings

3-(THIENYLOXY)PYRIDINES AND METHODS FOR THEIR PRODUCTION

SUMMARY AND DETAILED DESCRIPTION

The present invention relates to new 3-(thineyloxy)-pyridines and acid-addition salts thereof. More particularly, the invention relates to 3-(2-thienyloxy)pyridine and 3-(3-thienyloxy)pyridine and acid-addition salts thereof, and to a method for the production of the foregoing compounds.

The term "acid-addition salts" is intended to mean salts formed by the addition of an acid. Typical salts are as follows: methanesulfonate, pamoate, acetate, citrate, hydrochloride, sulfate, phosphate, benzoate, etc. Pharmaceutically acceptable acid-addition salts are preferred.

In accordance with the invention, the foregoing compounds of the invention can be prepared by reacting a compound of the formula

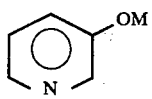
I with a compound of the formula

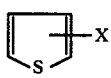
II in the presence of a copper catalyst, such as copper powder, copper-bronze or anhydrous cuprous salts, such as cuprous bromide and cuprous chloride, the preferred catalyst being copper-bronze; wherein M is a metal cation such as copper, cesium or potassium, preferably potassium and X is bromine or iodine, preferably iodine.

The foregoing reaction is preferably conducted in semi-polar, non-hydroxylic solvents or mixtures thereof having boiling points of over 100° C. Solvents such as diethylene glycol dimethyl ether (diglyme), triethylene glycol dimethyl ether (triglyme), tetraethylene glycol dimethyl ether (tetraglyme), diphenyl ether, 1-methyl-2-pyridone, 1-methyl-2-pyrrolidinone, 1-methyl-2-piperidinone and mixtures thereof may be employed. A preferred solvent is diglyme. While approximately equimolar quantities of the two reactants may be employed, a slight excess of either may be used if desired. The above reaction is generally conducted at a temperature of from 100° to 200° C. for a period of from 1 to 48 hours, preferably 150° to 180° C. for from 4 to 18 hours. The products may be isolated by conventional means such as distillation. In addition, the product may be isolated in the form of an acid-addition salt by reaction with an appropriate acid. The compounds of this invention are bases or the corresponding acid-addition salts of these bases. The bases and their acid-addition salts may be conveniently converted from one form to the other by using an appropriate acid or base.

The starting materials of the formulae I and II are known readily available compounds.

The compounds of the invention can exist in anhydrous form as well as in solvated, including hydrated, forms. In general, the hydrated forms and the solvated forms with phamaceutically-acceptable solvents are equivalent to the anhydrous or unsolvated form for the purposes of the invention.

The compounds of the invention are new chemical compounds of value as pharmacological agents. More specifically, they are cognition activators which are potentially useful in treating patients suffering from senility. In addition, the alerting and attention focusing quality of these compounds would make them useful in treating patients having certain learning disabilities, such as hyperactive children. Lastly, the compounds may be used in treating mental depression and in normal persons suffering from mental fatigue or boredom.

The compounds of this invention may be administered orally in the form of tablets, capsules, syrups, etc. or parenterally by being dissolved in an appropriate isotonic solution.

The activity of the compounds of this invention is determined by a test entitled "Facilitation of Low Base Line Self-Stimulation" which is based upon a procedure reported in "Life Sciences", 3 903 (1964).

Adult male albino rats are implanted with permanent electrodes in the medial forebrain bundle of the posterior hypothalamus, an area of the brain which yields intense reward when stimulated. After the animals recover from surgery, they are trained in a Skinner box to press a lever to stimulate their own brains electrically, i.e., to self-stimulate.

After the animals become expert at self-stimulation, the stimulating current is reduced individually for each rat to a level moderately above the reward threshold, which causes self-stimulation rates to decrease correspondingly. Training sessions are run each day under these reduced current conditions until response rates stabilize. The slow response rates generated by these conditions serve as the behavioral base lines. One then proceeds to test whether various treatments increase self-stimulation rates above these base lines. During all tests the self-stimulation behavior of the animals is continuously recorded graphically on cumulative recorders. Drugs, when administered, are given preferably by the oral route.

A drug is considered "active" if the baseline rates of self-stimulation of the animals are clearly augmented by the agent. Such increases in self-stimulation are considered a strong indication that the drug has stimulated the adrenergic reward systems of the brain, and therefore the drug may act favorably upon mental depression.

3-(2-thienyloxy)pyridine methanesulfonate exhibited an excitatory effect on self-stimulation at a dose level of 40 mg./kg. and the 3-(3-thienyloxy)pyridine methanesulfonate at dose levels of 20 mg./kg. and 40 mg./kg.

This invention is further illustrated by the following examples.

EXAMPLE 1

Potassium hydroxide pellets (85 percent), 33 g. is added to a solution of 48 g. of 3-hydroxypyridine in 250 ml. of diethyleneglycol dimethyl ether (diglyme). The mixture is stirred and heated slowly to 160° C. while the diglyme-water azeotrope is removed through a short Vigreaux column. The mixture is allowed to cool to 110° C. and 101 g. of 3-iodothiophene and 0.5 g. of copper-bronze catalyst is added. The mixture is stirred and heated at reflux (160° C.), allowed to cool and filtered through diatomaceous earth. The filtrate is evaporated at reduced pressure and the residue distilled. The portion boiling at 100°–150° C./10 mm. is collected and dissolved in anhydrous ether. The ether solution is filtered through a 30×2.5 cm. column of neutral alumina and then stored over potassium hydroxide pellets for 18 hours. The resulting solution is filtered, evaporated and distilled at reduced pressure to give 3-(3-thienyloxy)pyridine; b.p. 132°–135° C./10 mm.

A solution of 5.3 g. of 3-(3-thienyloxy)pyridine in 50 ml. of 2-propanol is mixed with a solution of 2.88 g. of methanesulfonic acid in 25 ml. of 2-propanol. The solution is evaporated and the residue is triturated with anhydrous ether to give crystals of the methanesulfonate salt which are collected and dried; m.p. 119°–120.5° C.

EXAMPLE 2

By substituting 99 g. of 2-iodothiophene for the 3-iodothiophene in Example 1, there is obtained 3-(2-thienyloxy)pyridine; b.p. 120°–122° C./10 mm.

A solution of 5.0 g. of 3-(2-thienyloxy)pyridine in 25 ml. of 2-propanol is added to a solution of 2.4 g. of methanesulfonic acid in 10 ml. of 2-propanol. The solution is evaporated at reduced pressure and the residue is triturated with anhydrous ether. The crystals of the methanesulfonate salt are collected and recrystallized from 2-propanol-ether; m.p. 116°–118° C.

I claim:

1. A compound selected from the group consisting of 3-(2-thienyloxy)pyridine, 3-(3-thienyloxy)pyridine and pharmaceutically acceptable acid-addition salts thereof.

2. The compound of claim 1 having the name 3-(2-thienyloxy)pyridine methanesulfonate.

3. The compound of claim 1 having the name 3-(3-thienyloxy)pyridine methanesulfonate.

4. A process for the preparation of a compound of claim 1 which comprises reacting a compound of the formula

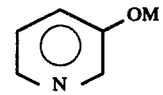

with a compound of the formula

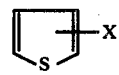

in the presence of a copper-bronze catalyst wherein M is potassium and X is iodine.

* * * * *